United States Patent [19]

Bao et al.

[11] Patent Number: 5,263,985
[45] Date of Patent: Nov. 23, 1993

[54] BONE GROWTH STIMULATOR

[75] Inventors: Qi-Bin Bao, Livingston; John H. Dumbleton; Paul A. Higham, both of Ringwood, all of N.J.

[73] Assignee: Pfizer Hospital Products Group, Inc., New York, N.Y.

[21] Appl. No.: 979,346

[22] Filed: Nov. 20, 1992

Related U.S. Application Data

[63] Continuation of Ser. No. 567,424, Aug. 14, 1990, abandoned.

[51] Int. Cl.$^5$ ............................................... A61F 2/28
[52] U.S. Cl. ..................................... 623/16; 623/66
[58] Field of Search ..................... 623/16, 18, 11, 66

[56] References Cited

U.S. PATENT DOCUMENTS 4,330,891 5/1982 Branemark et al. ................. 623/16
4,988,358 1/1991 Eppley et al. ........................ 623/16

FOREIGN PATENT DOCUMENTS 9001955 3/1990 PCT Int'l Appl. .

OTHER PUBLICATIONS

"Contributions of negatively charged chemical groups to the surface-dependent activation of human plasma by soluble dextran derivatives" by J. M. Nigretto et al. Published by Butterworth & Co. 1989.

"Charged Beads Stimulate Bone Formation" by M. Krukowski et al., from 39th Annual Meeting, Orthopedic Research Society, Feb. 1-4, 1988.

"Charged Beads: Generation of Bone and Giant Cells" by M. Krukowski et al. 1977.

"Charged Beads and Osteogenesis" by M. Krukowski & P. Osdoby, Washington University.

"Various Forms of Crosslinked Dextran Gel as Surface Wound Covering Materials" by Paul Wang, In Material Research Soc. Symp. Proc. vol. 110 1989 pp. 377-386.

"Initiation and Enhancement of Bone Formation" by J. Triffitt in Acta Orthopedic Scand. vol. 58, 1987, pp. 673-684.

"Experimental Heterotopic Bone Formation Induced by Bone Morphogenetic Protein and Recombinant Human Interleukin-1B" by P. Mahy and M. Urist, in Clinical Orthopaedics & Related Research, No. 237 Dec. 1988.

"Study of the osteoconductive properties of bioactive glass fibers" by Pazzäglia et al. in Journal of Biomedical Materials Research, vol. 23, 1989, pp. 1289-1297.

"Periosteal Bone Formation Elicted by Partially Purified Bone Morphagenetic Protein" by H. Nakahara et al, in Clinical Orthopedics & Related Research, No. 239, Feb. 1989, pp. 299-305.

"A Bovine Low Molecular Weight Bone Morphogenetic Protein (BMP) Fraction" by M. Urist et al., in Clinical Orthopaedics & Related Research, No. 162, Jan.-Feb. 1982, pp. 219-232.

"Interaction Between Primary Bone Cell Cultures and Biomaterials" in Biomaterials & Clinical Applications, 1987 pp. 579-602 by J. Davies et al.

Proposal by M. Krukowski et al. to Washington University.

*Primary Examiner*—David Isabella
*Attorney, Agent, or Firm*—Peter C. Richardson; Lawrence C. Akers; Raymond W. Augustin

[57] ABSTRACT

An implantable material for promoting bone growth has a microporous structure exhibiting an average pore size of at least 30 Å. The porous biomaterial is capable of retaining macromolecules having a molecular weight of at least 15,000 and up to 500,000.

3 Claims, No Drawings

BONE GROWTH STIMULATOR

This is a continuation of application Ser. No. 07/567,424, filed on Aug. 14, 1990 now abandoned.

BACKGROUND OF THE INVENTION

1. Field of the Invention

This invention relates to bone growth stimulation. More particularly, the invention relates to the use of dextran beads having a controlled pore size to stimulate bone and tissue growth.

2. Description of the Prior Art

In recent years, substantial research work on induced bone growth or osteogenesis has been conducted due to its clinical significance. Among all the different efforts, two separate but related approaches have brought most attention either because of their success in solving orthopedic problems or because of their considerable interest in the biology and applied science of osteoinduction. The first consists of clinical investigations of electric effect on inducing new bone formation. The second consists of biochemical investigations into bone growth, coupling, osteogenesis factors and a bone morphogenetic protein fraction.

The first approach, which has been documented at least a century ago, is to apply an electric field to stimulate and regulate osteogenesis. During the last forty years, more reports have shown that the cathode stimulates osteoinductive activity in both animal tests and clinical cases. Several studies have revealed that certain materials, such as neurones, myoblasts, neutral crest cells, epithelial cells, fibroblasts and osteoblasts migrate towards the cathode in the electric field. It could be one or a group of these materials, or some other unidentified materials, that play an important role in the process of bone regeneration.

The second approach, which started at a later time but has gained considerable attention recently, concentrates on identifying and isolating osteoinduction factors. Bone morphogenetic protein and human skeletal growth factor are the two osteoinductive proteins which have been isolated and characterized. Studies have shown that implantation of these proteins foster new bone formation.

More recently, researchers have applied charged dextran beads to enhance new bone formation. The unique characters of the dextran charged beads, their large porosity, large surface area, different charged groups and their affinity to different proteins have given some promising results. These results were reported at the 24th Annual Meeting of the Orthopaedic Research Society between Feb. 1 and 4, 1988 and published in the article "Charged Beads: Generation of Bone and Giant Cells" in the Journal of Bone & Mineral Research, 1988.

In the prior art study, three different types of Sephadex dextran beads made by Pharmacia, Inc. were used without any pretreatment. These beads are made from polyglucose dextran crosslinked with epichlorohydrin. The charged groups for producing the negative or positive charge are attached to glucose units in the matrix by stable ether linkages. The beads were suspended in Tyrode's salt solution (buffered at pH=7.3) and UV sterilized. The chemical and physical properties of these beads are listed in Table 1. The "fractionation range" refers to the ability of the beads to separate proteins having the stated molecular weights (MW).

TABLE 1

| Bead | Bead Charge | Charge Group | Counter Ion | Fractionation Range (MW) Globular Proteins |
| --- | --- | --- | --- | --- |
| G-25 | No | Neutral | No | 1000–5000 |
| DEA-A-25 | Positive | Weak Base Diethylaminoethyl | $Cl^-$ | <30000 |
| CM-C-25 | Negative | Weak Acid Carboxymethyl | $Na^+$ | <30000 |

In this study, only the negatively charged CM-C-25 beads displayed an osteoinductive effect. The study concluded that the negative electrical charge stimulated bone growth.

Use of charged beads to promote new bone formation may stem from one or both of the electric field inducing effect and the osteoinductive factors effect. Although quite a few studies have been conducted to investigate the effect of surface charge of the biomaterials on the bioactivity, very little effort has been taken in the study of the porosity effect of the biomaterials in the osteogenesis process.

Biomaterials with osteoinductive activity can be used not only to promote the healing of defective or fractured bone, but also to improve the integration of an existing implant with the surrounding tissue if the existing implant is coated with the bioactive materials. For the latter application, an interfacial bond of biomaterial with adjacent tissue will be the key issue to the success of implantation.

In order to understand the mechanism of biomaterial induced osteogenesis, a brief consideration of bone structure is essential. Bone is a specialized connective tissue comprising cells and an extracellular matrix (ECM). One type of cell, the osteoblast, is responsible for the fabrication of ECM. The ECM comprises organic and inorganic components. The organic component which weighs about 35% of the total weight is composed predominantly (95%) of Type I collagen. The remainder (5%) is a complex mixture of non-collagenous proteins and other macromolecules. Among these proteins, several of them, such as Bone Morphogenetic Protein (BMP), human Skeletal Growth Factor (hSGF) and some other growth factors, are known to increase cell replication and have important effects on differentiated cell function. However, little is understood of the precise modes of action of these macromolecules. The inorganic component of bone ECM is a complex calcium hydroxyapatite, more complex than the stoichiometric formula for hydroxyapatite, $Ca_{10}(PO_4)_6(OH)_2$, would suggest.

Due to the important role that osteoblasts and some osteoinductive factors play in the osteogenesis process, it is the hope that any biomaterials applied will have the capability either to colonize and concentrate the osteoinductive macromolecules, or to let the osteoblasts migrate towards the surface of these biomaterials. The unique properties of dextran beads have made them a good candidate for an osteoinductive material.

First, charging the beads offers an electric environment in the body when implanted, the same effect as an electrode can offer. Second, the different charged group and different porosity of the beads makes it possible to selectively bind to certain proteins with specific molecular weight and charge. Charged beads have been employed to separate proteins based on their different molecular weight and affinity to the beads. This characteristic, if the correct bead is chosen, makes it possible for the bead to bind and concentrate certain osteoinductive factors near the beads.

The actual osteogenesis induced by biomaterials is a complex and regulated process and the exact mechanism of it is, at the moment, not well understood. Several hypotheses have been proposed trying to correlate the in vivo/in-vitro results with the biomaterial properties, such as steric charge, porosity, particle size and the nature of the materials, etc. Among all these hypotheses, the explanation appears to lie more in the interaction between the biomaterials and the osteoinductive factors, which include Bone Morphogenetic Protein (BMP), human Skeletal Growth Factor (hSGF) and some other growth factors. The interaction could actually result in colonizing, concentrating and finally activating the osteoinductive factors involved. It has been known that some biological molecules, BMP in particular, are responsible for inducing the new bone formation. Another hypothesis emphasizes more the interaction of the biomaterials and bone cells, particularly osteoblasts, which are responsible for the fabrication of the ECM. It has been found in vitro that osteoblasts migrate towards different biomaterials at different rates and attach onto them with different morphologies depending on the surface charge of the biomaterials. However, the correlation of bone cell morphology and the osteoinductive activity is still not clear. It is also not understood that if the different cell morphology is the direct effect of the surface charge or if the effect is indirect. Due to the fact that the rate of cell migration towards the biomaterials is much slower than the rate of chemical or steric charge interaction between the macromolecules or other organic or inorganic chemicals in the physiological environment and the biomaterials, the surface charge of the biomaterials could be altered before the cells migrate and attach to the biomaterials.

In the prior art, the investigation has been only concentrated on the charge effect. It has indeed been found that osteoblast migratory morphology and extracellular matrix synthesis are sensitive to the charge of the biomaterial which is colonized. Very little attention has been paid to the effect of the porosity of the biomaterial used either as implants or as a coating on the metal implants. Because it has been known that osteoblasts colonizing a biomaterial are able to span pore openings on the surface of macroporous, bioactive substrates and the fact that the dimension of the osteoblasts is much bigger than that of the porosity studied in this art, the porosity of the beads investigated in this art probably would have little direct effect on the osteoblast migratory morphology. However, the indirect effect on osteoblast migratory morphology, which is caused by the fact that various macromolecules have different binding capability to the different pore size beads, is still possible. Because most osteoinductive macromolecules have the molecular weight range between 15,000 to 30,000, the porosity of the biomaterials used in the implants will have significant effect on the binding capability of these osteoinductive macromolecules.

The porosity of the dextran beads depends on the degree of cross-linking and the concentration of the charged groups attached to them. Sephadex A and C type beads are derived from the G-type beads by introducing the charged groups to the matrix. Although the numbers of A and C beads still remain the same as the G bead (A-25 and C-25 are made from G-25, A-50 and C-50 are made from G-50), the porosities of wet beads change significantly due to the increase of swelling capability by introducing the charged groups. Each Sephadex bead has a different molecular weight range over which molecules can be fractionated. Molecules with molecular weight above the upper limit of this range, the exclusion limit, are totally excluded from the gel. Table 2 gives the fractionation ranges for the different Sephadex dextran beads.

TABLE 2

| | PROPERTIES OF SEPHADEX | | |
|---|---|---|---|
| | Fractionation Range (MW) | | |
| Sephadex Type | Peptides and Globular Proteins | Dextrans | Bed Volume ml/g dry Sephadex |
| G-25 | 1000–5000 | 100–5000 | 4–6 |
| G-50 | 1500–30000 | 500–10000 | 9–11 |
| G-75 | 3000–80000 | 1000–50000 | 12–15 |
| G-100 | 4000–150000 | 1000–100000 | 15–20 |
| A-25, C-25 | <30000 | | 7–10 |
| A-50, C-50 | 30000–150000 | | vary with pH |

While dextran beads have been discussed, other polymers having properties similar to those shown above can be used. For example, an entire orthopedic implant can be made of such polymers (with the above properties) or an existing orthopedic implant can be coated with such polymers to form an osteoinductive surface thereon.

SUMMARY OF THE INVENTION

It is an object of this invention to provide an implantable material for promoting bone growth.

It is a further object of this invention to provide an implantable material which has a porous structure with a pore size capable of retaining molecules of osteoinductive proteins therein.

It is yet another object of this invention to provide an implantable material which can be used as a carrier for osetoinductive factors.

These and other objects are achieved by an implantable biomaterial having a porous surface exhibiting an average pore size of at least 30 Å. This pore size is capable of retaining molecules having a molecular weight of at least 15,000 and up to 500,000. At the high end of the molecular weight range, the average pore size is about 500 Å. Dextran beads exhibit this porosity and may be used as the biomaterial. Clearly, other polymers having similar pore sizes and capable of retaining molecules with the range stated above can also be used.

This biomaterial having a porous surface is used to determine the osteoinductive characteristics of materials as they relate to the ability of the material to bind osteoinductive macromolecules. The materials are either uncharged, negatively charged or positively charged.

This biomaterial may be Sephadex type dextran beads as indicated above. All beads having a pore size capable of binding with macromolecules with a molecular weight of more than 5000 showed osteoinductive capabilities. This was true regardless of charge.

The biomaterial may be modified to carry osteoinductive factors by impregnating the biomaterial with osteoinductive factors by placing it in a solution or slurry containing these factors prior to implantation. Alternately, the biomaterial may be directly implanted at a bony site where the porous biomaterial will bond and inherently act to concentrate the osteoinductive factors naturally present at the site.

The porous biomaterial which acts to promote bone growth can be formed into and used as an implantable device. The biomaterial can also be used as a coating material for an existing implantable device without altering the bulk properties of the original device. The osteoinductive characteristic of the porous biomaterial not only can promote the healing of defective or fractured bone but also can improve the fixation of an existing implant by being used as a coating on the same.

DESCRIPTION OF THE PREFERRED EMBODIMENT

The invention will now be described in further detail with reference being made to the following example. It should be recognized, however, that the example is given as being illustrative of the present invention and is not intended to define or limit the spirit and scope thereof.

EXAMPLE

Two neutral dextran beads (G-25 and G-75) with different pore size purchased from Pharmacia were used. The beads were washed with 0.1N NaOH to remove any impurities then balanced with pH buffer. Sterilization took place by autoclaving the beads at 120° C. for 30 minutes. The chemical and physical properties of these two beads, along with the two charged beads, are listed in Table 3.

TABLE 3

| Bead | Bead Charge | Charge Group | Counter Ion | Fractionation Range (MW) Globular Proteins |
|---|---|---|---|---|
| G-25 | No | Neutral | No | 1000–5000 |
| G-75 | No | Neutral | No | 3000–80000 |
| DEAE-A-25 | Positive | Weak Base Diethyl-aminoethyl | $Cl^-$ | <30000 |
| CM-C-25 | Negative | Weak Acid Carboxy-methyl | $Na^+$ | <30000 |

A 6.0 mm hole was drilled into the distal femoral epiphysis of eighteen rabbits. The hole was drilled from the medial surface toward, but not extending through, the lateral surface. The right limb of each animal was used as a control and the defect filled with neutral charged dextran beads (G-25). The left drill hole was filled with the neutral beads with a larger pore, G-75.

The materials were implanted for four weeks, at which time the animals were sacrificed. The condyles of each limb were cut into lateral and medial halves. The medial and lateral halves of each femur was decalcified and embedded in methylmethacrylate. A histological examination was performed and the results are shown in Table 4.

TABLE 4

HISTOLOGY RESULTS

| Bead Injected | Tissue Ingrowth* | Number of Sections Examined |
|---|---|---|
| G-25, Uncharged | − | 6 |
| G-75, Uncharged with Large Pore Size | + | 2 |

*−, only soft tissue ingrowth
+, good to excellent bone ingrowth

From the prior art data, it is very easy to conclude that it is necessary to have electric charged group in the beads for osteoinductive activity. However, if the physical properties of the different beads are examined in view of the results of Example 1, it is found that this conclusion is probably incorrect. It is very easy to assume that G-25 beads would have the same pore size as the A-25 and C-25 beads because all A-25 and C-25 beads are derived from G-25 beads by attaching the charged groups to them and because they have the same cross-link density. However, the actual pore size of wet G-25 beads is quite different from that of A-25 and C-25 beads, as we can see from Table 2, because attaching the charged groups to the polymer increases the swell capability of the beads. The fractionation range for G-25 is only 1000 to 5000, while the fractionation range for both A-25 and C-25 is up to 30,000. It is improper, therefore, to use G-25 beads as a control to compare them with A-25 and C-25 beads for electric charge effect because there is something (porosity) other than electric charge which is also very different among these beads. It is not surprising that the G-25 beads did not have any osteoinductive activity in the prior art because most, if not all, osteoinductive proteins have a molecular weight larger than 5000.

Due to the significant porosity difference among these charged and uncharged -25 beads, G-75 beads, which have the same order of pore size as A-25 and C-25 beads, were chosen to see how significantly the porosity contributes to the osteoinductive process. In this case, we can differentiate the pore size effect from the electric charge effect. Because G-25 and G-75 beads are made of the same polymer, any difference observed in osteoinductive activity should be attributed to the pore size effect. At the same time, the result of G-75 beads also can be used to compare with those beads used in the prior art to see how the different bead charges affect the osteogenesis.

The present study demonstrated that significant bead-associated new bone formation was observed with the uncharged G-75 beads, while there was no evidence of bead-associated new bone with the uncharged G-25 beads. This indicates that the microporosity plays a very important role in the biomaterial induced osteogenesis process. This invention, however, does not intend to indicate that microporosity is the only requirement of the osteoinductive activity for a biomaterial. The capability of interaction between the biomaterial and the molecules and living cells is still very important. It is very difficult to use steric charge effect to explain the binding between the neutral or positively charged dextran beads and the charged osteoinductive factors. However, other intermolecular forces including dipole forces, hydrogen bonds and hydrophobic bonds are still available for the interaction between the biomaterials and the osteoinductive factors and living cells. The present study shows that the appropriate microporosity of a biomaterial, either used alone or used as a coating, can promote osteoinductive activity of the material.

Because most known biologically active macromolecules in ECM have a molecular weight between 15,000 to 30,000, with the exception of hSGF with a molecular weight of around 80,000, it will be expected that the minimum average microporosity should be large enough to accommodate those macromolecules. The upper limit of the microporosity would have less restriction than the low limit in binding these macromolecules. Although only one large porosity dextran bead (G-75) was used, based on the knowledge of basic biochemistry and biology, a conclusion can be extrapolated that the appropriate pore size for a bioactive material in the osteogenetic applications should have the molecular fractionation range of MW 15,000 to 500,000, which corresponds approximately to the size of between 30 Å and 500 Å.

While several embodiments and examples of the present invention have been described, it is obvious that many changes and modifications may be made thereunto, without departing from the spirit and scope of the invention.

I claim:

1. A process for promoting tissue growth around a prosthetic implant comprising:
    coating the prosthetic implant with a biomaterial having a neutral surface charge and having a microporous structure exhibiting interconnected pores with an average pore size of between 3 nm and 50 nm, such that said biomaterial has a binding effect to osteoinductive protein molecules within said pores; and
    implanting said prosthetic implant in the body adjacent tissue and promoting bonding of osteoinductive molecules having a molecular weight of at least 15,000 and up to 500,000 within said pores, thereby inducing new bone growth at the implant site.

2. The process as set forth in claim 1 wherein the biomaterial is a wetted dextran bead.

3. A process for promoting tissue growth comprising:
    forming a prosthetic implant from a multiplicity of uncharged dextran beads having, in the wet state, a neutral surface charge and a microporous structure exhibiting interconnected pores with an average pore size of between 3 nm and 50 nm, such that said biomaterial has binding effect to osteoinductive protein molecules within said pores; and
    implanting said prosthetic implant in the body adjacent tissue and promoting bonding of osteoinductive molecules having a molecular weight of at least 15,000 and up to 500,000 within said pores, thereby inducing new bone growth at the implant site.

* * * * *